United States Patent [19]

Eckell et al.

[11] 4,213,884

[45] Jul. 22, 1980

[54] MANUFACTURE OF A HIGHLY CONCENTRATED AQUEOUS SOLUTION OF A DICARBOXYLIC ACID DIAMINE SALT AND A NYLON PRECONDENSATE

[75] Inventors: Albrecht Eckell, Frankenthal; Paul Matthies, Heidelberg; Georg Pilz, Neustadt; Rudi-Heinz Rotzoll, Limburgerhof, all of Fed. Rep. of Germany

[73] Assignee: BASF Aktiengesellschaft, Fed. Rep. of Germany

[21] Appl. No.: 913,641

[22] Filed: Jun. 8, 1978

[30] Foreign Application Priority Data

Jun. 27, 1977 [DE] Fed. Rep. of Germany ....... 2728817

[51] Int. Cl.² .............. C08G 69/28; C07C 51/52
[52] U.S. Cl. .............. 260/29.2 N; 260/501.2; 528/335; 528/346; 528/349
[58] Field of Search .............. 528/335; 260/501.2, 260/29.2 N

[56] References Cited

U.S. PATENT DOCUMENTS

| | | | |
|---|---|---|---|
| 2,923,699 | 2/1960 | Indest et al. | 528/335 |
| 3,185,672 | 5/1965 | Clemo et al. | 528/335 |
| 3,476,713 | 11/1969 | Dorsey | 528/335 |
| 3,502,624 | 3/1970 | Flack et al. | 528/335 |
| 3,952,051 | 4/1976 | Ogawa et al. | 528/335 |
| 4,131,712 | 12/1978 | Sprauer | 528/335 |

FOREIGN PATENT DOCUMENTS

| | | | |
|---|---|---|---|
| 674954 | 7/1952 | United Kingdom | 528/335 |
| 1018653 | 1/1966 | United Kingdom | 528/335 |

*Primary Examiner*—Harold D. Anderson
*Attorney, Agent, or Firm*—Keil & Witherspoon

[57] ABSTRACT

A process for the manufacture of a highly concentrated aqueous solution of a salt of a dicarboxylic acid and a diamine, as well as of a nylon precondensate, by reacting an alkanedicarboxylic acid of 6 to 12 carbon atoms and a diamine of the formula $NH_2RNH_2$, where R is alkylene of 6 to 12 carbon atoms or is

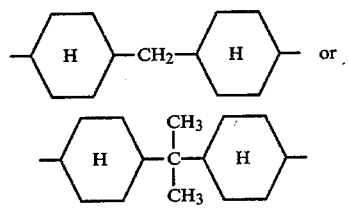

An aqueous solution, of lower concentration, of a salt of a dicarboxylic acid and a diamine, containing an appropriate dissolved excess of the particular dicarboxylic acid, is reacted with the particular diamine in the molten state, in an equivalent amount to the dissolved dicarboxylic acid, the reaction being carried out under superatmospheric pressure and the final reaction temperature being kept at from 140° to 210° C. The solution obtained is used for the manufacture of a nylon.

6 Claims, No Drawings

MANUFACTURE OF A HIGHLY CONCENTRATED AQUEOUS SOLUTION OF A DICARBOXYLIC ACID DIAMINE SALT AND A NYLON PRECONDENSATE

The present invention relates to a process for the manufacture of a highly concentrated aqueous solution of a salt of a dicarboxylic acid and a diamine, optionally including oligomeric nylon precondensates, by reacting an alkanedicarboxylic acid of 6 to 12 carbon atoms and a diamine of the formula NH$_2$RNH$_2$, where R is alkylene of 6 to 12 carbon atoms or is

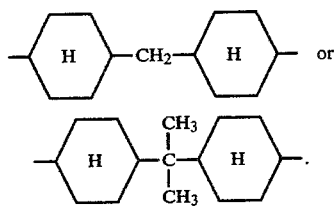

In the conventional industrial manufacture of a nylon from a dicarboxylic acid and a diamine, the starting material is, as a rule, an aqueous solution of a salt of the dicarboxylic acid and the diamine. As disclosed in British Patent 674,954, German Pat. No. 1,060,139 and German Published Application DAS 1,158,257, the salt solution used is in general of from 45 to 70 percent strength by weight. However, before the actual polycondensation it is necessary substantially to remove the excess water from the salt solution. This has the disadvantage that large amounts of liquid have to be transported and, furthermore, substantial amounts of energy have to be consumed to remove the water.

In order to avoid the presence of an unnecessary amount of water, an attempt has also already been made to carry out the manufacture of a nylon directly from the liquid starting materials, e.g. molten adipic acid and molten hexamethylenediamine. Such processes are disclosed in, for example, British Pat. No. 1,018,653 and Belgian Pat. No. 640,369. Apart from the fact that molten adipic acid undergoes chemical modification, for example by decarboxylation and by anhydride formation, the metering of the starting materials presents substantial problems, particularly as precise metering is necessary in order to maintain an equivalent ratio of starting materials.

German Laid-Open Application DOS 2,403,178 discloses the production of a crystalline salt from a dicarboxylic acid and a diamine by neutralizing a salt solution, containing dicarboxylic acid, with the particular diamine. However, it prescribes that the temperature should not exceed 80° C.

It is an object of the present invention to provide a starting solution for the manufacture of a nylon from a dicarboxylic acid and a diamine, which solution is easy to handle and contains very little water, and to utilize the thermal energy contained in the starting solution.

We have found that this object is achieved by a process for the manufactore of a highly concentrated aqueous solution of a salt of a dicarboxylic acid and a diamine, as well as of a nylon precondensate, which comprises reacting an alkanedicarboxylic acid of 6 to 12 carbon atoms and a diamine of the formula NH$_2$RNH$_2$, where R is alkylene of 6 to 12 carbon atoms or is

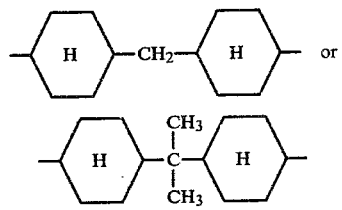

wherein an aqueous solution, of lower concentration, of a salt of such a dicarboxylic acid and such a diamine, containing an appropriate dissolved excess of the particular dicarboxylic acid, is reacted with the particular diamine in the molten state, in an equivalent amount to the dissolved dicarboxylic acid, the reaction being carried out under superatmospheric pressure and the final reaction temperature being kept at from 140° to 210° C.

The novel process has the advantage that a very concentrated aqueous starting solution for the manufacture of a nylon, which solution does not require further concentrating, is obtained directly. It has the further advantage that a starting solution in which the heat of neutralization contained herein is utilized for the polycondensation is obtained. Finally, it has the advantage that metering and mixing the starting materials is simple.

In view of German Laid-Open Application DOS 2,403,189 it did not appear to be advisable to exceed 80° C. when neutralizing the dicarboxylic acid with the diamine, since products unusable for polycondensation were to be expected at a higher temperature.

According to the invention, one of the starting materials is an alkanedicarboxylic acid of 6 to 12 carbon atoms, straight-chain α,ω-dicarboxylic acids with this number of carbon atoms being preferred. Examples of suitable dicarboxylic acids are adipic acid, suberic acid, azelaic acid, sebacic acid, decanedicarboxylic acid and dodecanedicarboxylic acid. Adipic acid and sebacic acid are industrially particularly important.

The further starting material is a diamine of the formula NH$_2$RNH$_2$, where R is alkylene of 6 to 12 carbon atoms or is

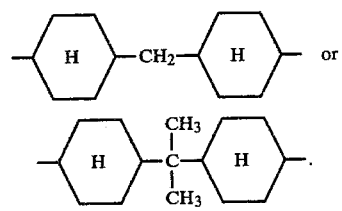

The use of straight-chain α,ω-alkanediamines of 6 to 12 carbon atoms is particularly preferred. Examples of suitable diamines are hexamethylenediamine, octamethylenediamine, decamethylenediamine, dodecamethylenediamine, bis-(4-aminocyclohexyl)-methane and 2,2-bis-(4-aminocyclohexyl)-propane. Hexamethylenediamine is industrially particularly important. Accordingly, preferred products are solutions of salts and nylon precondensates which are derived from adipic acid or sebacic acid and hexamethylenediamine.

The process starts from a less concentrated aqueous solution of a salt of a dicarboxylic acid and a diamine, containing an appropriate dissolved excess of the particular dicarboxylic acid. It is advantageous to use a solution which contains from 40 to 65 percent by weight, especially from 50 to 65 percent by weight, of the particular salt, based on the sum of salt and water. The amount of dissolved dicarboxylic acid depends on the desired final concentration of the highly concentrated aqueous solution to be prepared.

In one preferred embodiment, solid dicarboxylic acid is dissolved in a less concentrated salt solution, as a rule at from 60° to 110° C. The resulting salt solution containing free dicarboxylic acid is then reacted with an equivalent amount, based on the dissolved dicarboxylic acid, of molten diamine. It is advantageous to ensure that the pH corresponds to the equivalence point of the particular salt to be prepared. For example, the equivalence point of hexamethylenediammonium adipate corresponds to pH 7.62 and the equivalence point of hexamethylenediammonium sebacate to pH 7.5, measured in 10% strength aqueous solution at 25° C. Advantageously, the reaction is carried out in a mixing zone, by first adding a slightly less than equivalent amount of molten diamine and then adjusting the pH precisely by further addition of molten diamine. In order to compensate for the loss of diamine occurring during polycondensation, the diamine is as a rule used in excess, for example of up to 1.5 mole %.

According to another preferred embodiment, solid dicarboxylic acid is first dissolved in an aqueous solution of a less than equivalent amount of the diamine. This gives a solution of the salt of the dicarboxylic acid and diamine, which contains an excess dissolved amount of dicarboxylic acid. Naturally, the ratios used are selected so that the salt solution has the above concentration and the excess amount of dicarboxylic acid corresponds to the desired final concentration of the aqueous solution. Advantageously, the dicarboxylic acid is dissolved at from 60° to 110° C., as a rule under atmospheric pressure. The resulting salt solution containing free dicarboxylic acid is then reacted with an equivalent amount, based on dissolved dicarboxylic acid, of molten diamine. This reaction is advantageously carried out as described for the above method.

It is an essential aspect of the invention that the reaction of the dissolved dicarboxylic acid with molten diamine is carried out under superatmospheric pressure, advantageously at from 2 to 15 bars. An appropriate pressure results automatically from the autogenous pressure and can be further increased by adding small amounts of nitrogen, to prevent the solution from boiling. It is a further essential feature of the invention that the final temperature of the neutralization is from 140° to 210° C., a temperature of from 160° to 200° C. being particularly preferred.

The aqueous solution obtained contains a salt of the dicarboxylic acid and the diamine and may also contain oligomeric nylon precondensates resulting from incipient polycondensation. The reaction of the amino groups with the carboxyl groups to form amide groups may be up to 50%, for example from 20 to 45%.

The aqueous solution produced advantageously contains from 70 to 90 percent by weight, especially from 80 to 90 percent by weight, of a salt of a dicarboxylic acid and a diamine, plus nylon precondensates.

The very concentrated aqueous solution, prepared according to the invention, of a salt, with or without nylon precondensates, derived from a dicarboxylic acid and a diamine, is exceptionally suitable for the manufacture of a nylon by condensation. The condensation can be carried out batchwise or continuously. Examples of suitable condensation processes are described in German Published Application DAS 1,495,087, British Pat. No. 1,159,151, British Pat. No. 674,954, German Pat. No. 1,060,139 and German Laid-Open Application DOS 2,417,003. It is particularly advantageous to use the aqueous solution of the invention for the condensation without first removing the heat of neutralization. Heat losses resulting from the apparatus are insignificant in this context.

It is also possible to utilize part of the heat of neutralization for dissolving the dicarboxylic acid in the less concentrated salt solution.

Nylons manufactured from the solutions according to the invention may be used for the manufacture of articles produced from the melt, e.g. filaments, fibers, moldings, sheets or coatings.

The Examples which follow illustrate the process of the invention. Percentages are by weight.

EXAMPLE 1

5,250 g of nylon salt (hexamethylenediammonium adipate) were dissolved in 3,450 g of water in a 40 liter stirred autoclave, whilst heating at 95° C. 8,025 g of solid adipic acid were added gradually to the resulting 60.3% strength nylon salt solution, whilst stirring at 90°–95° C., and were dissolved therein. The autoclave was flushed with nitrogen and sealed. The contents were heated to 100° C., resulting in an autogenous pressure of 2 bars. 6,375 g of molten hexamethylenediamine at 100° C. were forced into the autoclave from a feed vessel by means of nitrogen pressure, in the course of 2 minutes, with the stirrer running. The temperature of the 85 percent strength by weight nylon salt solution rose due to the heat of neutralization liberated and reached 162° C. 2 minutes after adding the hexamethylenediamine. The pressure transiently rose to 4 bars during addition of the hexamethylenediamine and fell to 3 bars by the end of the addition.

Nylon 6,9 and nylon 10,6 salt solutions were obtained by the same method as that described above.

EXAMPLE 2

This Example illustrates the utilization of part of the heat of neutralization for dissolving the dicarboxylic acid.

292 g of solid adipic acid were introduced, at 20° C., into a glass flask equipped with a stirrer, reflux condenser, thermometer and dropping funnel. The flask was dipped into a waterbath at 75° C., acting as protective heating; immediately thereafter, a solution, kept at 90° C. in a dropping funnel, of 75 g of hexamethylenediamine in 92 g of water was added in the course of 20 seconds, whilst stirring. After 2 minutes, a clear solution, having a temperature of 69° C., was obtained. This solution contained 37% of nylon salt, 43% of adipic acid and 20% of water. The further reaction was carried out as described in Example 1.

EXAMPLE 3

The nylon salt solution obtained in Example 1 was polycondensed without first cooling it. It was heated to 275° C. in the course of 3½ hours, whilst keeping the pressure at 19 bars by blowing off steam. After reaching 275° C., the solution was let down to atmospheric pressure in the course of 1 hour and then post-condensed for 1 hour at up to 275° C. The product was forced out of the autoclave by nitrogen pressure and the strand of molten material was cooled in a waterbath and was granulated. The resulting nylon 6,6 had a relative viscosity of 2.54, measured in 1% strength solution in 96% strength sulfuric acid, and contained 54 milliequivalents/kg of acid groups and 76 milliequivalents/kg of basic groups.

We claim:

1. A process for the manufacture of highly concentrated aqueous solution of a salt of an alkanedicarboxylic acid of 6 to 12 carbon atoms and an alkane diamine of 6 to 12 carbon atoms which process consists essentially of:
    adding molten alkane diamine to an aqueous solution containing from about 40 to 65% by weight of said salt and containing an excess amount of the dicarboxylic acid at a temperature of from 60° to 110° C., the amount of said molten alkane diamine being equivalent to the amount of dissolved dicarboxylic acid, and
    allowing the final reaction temperature to rise to from 160° to 200° C. under super atmospheric pressure, whereby a highly concentrated solution containing from 70 to 90% by weight of said salt and a nylon precondensate of the salt is formed.

2. The process of claim 1, wherein the pressure is maintained at from 2 to 15 bars.

3. The process of claim 1, wherein a dicarboxylic acid is dissolved in an aqueous solution of a salt of the dicarboxylic acid with a diamine, and is then reacted with molten diamine.

4. The process of claim 1, wherein a part of the heat of neutralization is utilized to dissolve the dicarboxylic acid.

5. The process of claim 1, wherein the highly concentrated solution contains from 80–90% by weight of the salt and a nylon precondensate of the salt.

6. The process of claim 1, wherein the aqueous solution containing from about 40 to 65% by weight of said salt is prepared by mixing solid dicarboxylic acid with a less than equivalent amount of aqueous diamine, which aqueous salt solution is then reacted with molten diamine.